United States Patent
Wellman (10) Patent No.: US 6,585,733 B2
(45) Date of Patent: Jul. 1, 2003

(54) SURGICAL TREATMENT FOR ATRIAL FIBRILLATION USING RADIOFREQUENCY TECHNOLOGY

(75) Inventor: Parris S. Wellman, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/966,756

(22) Filed: Sep. 28, 2001

(65) Prior Publication Data

US 2003/0065319 A1 Apr. 3, 2003

(51) Int. Cl.$^7$ ............................................. A61B 18/18
(52) U.S. Cl. ............................. 606/41; 606/47; 606/50
(58) Field of Search ............. 606/41–52; 607/101–102, 607/122

(56) References Cited

U.S. PATENT DOCUMENTS

| | | | |
|---|---|---|---|
| 5,697,928 A | 12/1997 | Walcott et al. | 606/41 |
| 5,720,743 A * | 2/1998 | Bischof et al. | 606/32 |
| 5,904,711 A | 5/1999 | Flom et al. | 607/129 |
| 6,012,457 A | 1/2000 | Lesh | 128/898 |
| 6,079,414 A | 6/2000 | Roth | 128/898 |
| 6,161,543 A | 12/2000 | Cox et al. | 128/898 |
| 6,164,283 A | 12/2000 | Lesh | 128/898 |
| 6,237,605 B1 | 5/2001 | Vaska et al. | 128/898 |
| 6,245,064 B1 | 6/2001 | Lesh et al. | 606/34 |
| 6,251,109 B1 | 6/2001 | Hassett et al. | 606/45 |
| 6,311,692 B1 * | 11/2001 | Vaska et al. | 606/41 |
| 6,337,998 B1 * | 1/2002 | Behl et al. | 607/101 |
| 6,471,695 B1 * | 10/2002 | Behl | 606/32 |

OTHER PUBLICATIONS

Javier Roman–Gonzalez et al. "Collateral Tissue Injury Occurring During Intrapericardial Catheter Ablation in the Closed Chest Canine Model" North American Society for Pacing and Clinical Electrophysiology 22$^{nd}$ Annual Scientific Sessions, Hynes Convention Center, Boston, Massachusetts, USA 388 (May 2–5, 2001).

David E. Haines et al. "Rapid, Continuous and Transmural Linear Ablation With a Novel Bipolar Radiofrequency Ablation System" North American Society for Pacing and Clinical Electrophysiology 22$^{nd}$ Annual Scientific Session, Hynes Convention Center, Boston, Massachusetts, USA 279 (May 2–5, 2001).

* cited by examiner

Primary Examiner—Linda C. M. Dvorak
Assistant Examiner—David M. Ruddy
(74) Attorney, Agent, or Firm—Nutter McClennen & Fish LLP

(57) ABSTRACT

Ablation systems and methods for treating atrial fibrillation utilizing RF energy are provided. The system generally includes a first conductive member having a shape which defines a desired lesion pattern or a portion of a desired lesion pattern, and a second conductive member effective to transmit ablative radiation to the first conductive member. The first conductive member is adapted to be positioned on a first tissue surface, and the second conductive member is adapted to be positioned on a second, opposed tissue surface. In use, ablative radiation is transmitted from the second conductive member through the tissue to the first conductive member to form a lesion having the desired lesion pattern.

20 Claims, 7 Drawing Sheets

SURGICAL TREATMENT FOR ATRIAL FIBRILLATION USING RADIOFREQUENCY TECHNOLOGY

FIELD OF THE INVENTION

The present invention relates to instruments and methods for treating atrial fibrillation, and more particularly to a surgical instrument and method for ablating cardiac tissue using radiofrequency energy.

BACKGROUND OF THE INVENTION

Cardiac arrhythmias, such as atrial fibrillation, are a commonly occurring disorder characterized by erratic beating of the heart. The regular pumping function of the atria is replaced by a disorganized, ineffective quivering caused by chaotic conduction of electrical signals through the upper chambers of the heart. While medication can be an effective treatment for some cases, many patients are not responsive to medical therapies and require alternative treatment. As an alternative to medication, a surgical technique, known as the Maze technique, requires open chest surgery to strategically incise the atrial wall, and subsequently repair the incisions by suturing. The result of this surgery is to create scar tissue located along the incision lines and extending through the atrial wall to block electrical conductivity from one segment to another.

While the Maze procedure has proven effective in restoring normal sinus rhythm, it requires considerable prolongation of cardiopulmonary bypass and aortic crossclamp time, especially when performed in combination with other open heart procedures. Over the last decade, more simplified techniques have been proposed which replace surgical incisions with ablations, or scars, formed in the heart tissue. The various energy sources used in ablation technologies include cryogenic, radiofrequency (RF), laser, and microwave energy. The ablation devices are used to create tissue lesions in an affected portion of the heart in order to block electrical conduction.

One common ablation technique employs the use of a catheter that is introduced into the heart (e.g., intravascularly) to direct RF energy at specific areas of heart tissue found to be the source of the irregular rhythms. An electrophysiology (EP) study is first performed to discover the location and characteristics of the arrhythmia and, once the specific location is identified and mapped, RF energy is delivered to the tissue to ablate the tissue, thus forming a lesion that blocks electrical conduction. While minimally invasive techniques are usually preferred, the procedure is often performed in combination with other open heart procedures as a prophylactic to prevent post-operative onset of atrial fibrillation.

RF ablation techniques are typically successful in treating atrial fibrillation, however the A lesions must be well defined within the heart to be effective. The lesion must have a sufficient length, continuity and/or depth to interrupt or to block electrical conduction across the affected portion of the heart. This can be difficult to achieve without forming an incision in the atrium. In addition, if the energy is not uniformly transmitted to the target site, hot spots can form, possibly leading to severe tissue damage or blood coagulation (clots).

Accordingly, there exists a need for ablation instruments and procedures that produce uniform ablations on a retracted atria.

SUMMARY OF THE INVENTION

The present invention provides ablation systems and methods for treating atrial fibrillation utilizing RF energy. The ablation system generally includes two components: a first conductive component adapted to be placed on or adjacent to a first tissue surface, and a second conductive component adapted to be placed on or adjacent to a second, opposed tissue surface. Both components are effective to communicate with a source of ablative energy. The first component is shaped to conform to a desired lesion pattern, or portion of a lesion pattern. In use, ablative radiation is transmitted from the second component through the tissue to the first component to form the desired lesion pattern, or portion of a lesion pattern.

In one embodiment, the first component is an elongate conductive member and the second component is a tissue piercing element. The elongate conductive member is in communication with a source of ablative energy and is adapted to be positioned on a tissue surface. A plurality of openings, each having a specific diameter, are formed in the elongate conductive member. The openings can be spaced apart by a distance such that, together, the openings form a portion of a lesion pattern. The tissue piercing element, which is electrically isolated from the elongate conductive member, has a diameter less than the diameter of each opening in the conductive member, and is adapted to be deployed through each of the openings in the elongate conductive member. In use, the tissue piercing element is effective to transmit ablative energy through the tissue surface to the conductive member to form a lesion having a desired lesion pattern.

The tissue piercing element can include a proximal end and a distal end adapted to be selectively deployed into tissue through each of the plurality of openings. A first conductor element effective to communicate with a source of ablative energy can extend from the conductive member, and a second conductor element effective to communicate with a source of ablative energy can extend from the tissue piercing element. In a preferred embodiment, the tissue piercing element is an energy transmitting electrode and the elongate conductive member is a return electrode.

In another embodiment, an insulative coating is disposed around the circumference of each of the plurality of openings in the elongate conductive member, or alternatively such a coating is disposed around a portion of the tissue piercing element. The insulative coating is effective to electrically isolate the conductive member from the tissue piercing element.

In yet another embodiment, the elongate conductive member includes a top surface and a bottom, tissue contacting surface. The bottom surface can include an adhesive for selectively securing the elongate conductive member to tissue. The elongate conductive member can optionally be malleable to allow the conductive member to be formed into a desired shape to conform to the tissue on which it is placed, or to form a desired lesion pattern.

In other aspects according to the present invention, the tissue piercing element includes a flashback lumen extending between a fluid entry port formed on the distal end of the tissue piercing element and a fluid exit port formed on a proximal portion of the tissue piercing element. The flashback lumen is effective to indicate the position of the distal end of the tissue piercing element when inserted through one of the plurality of openings in the conductive member, thereby providing an indication of the penetration depth.

In another embodiment, the first component of the surgical ablation system is a return electrode and the second component is an energy transmitting electrode. The return electrode is movable between a first, retracted position and a second, open position wherein the return electrode assumes a substantially circumferential shape. The energy transmitting electrode is effective to transmit ablative radiation between intervening tissue and the return electrode member to form a substantially circumferential lesion pattern. The system can also include an introducer element having an inner lumen formed therein and being adapted to receive the return electrode in the retracted position.

Methods of ablating tissue are also provided. In one embodiment, a conductive member is provided having a plurality of openings and being effective to communicate with a source of ablative energy. A tissue piercing element electrically isolated from the conductive member and in communication with the source of ablative energy is also provided. The conductive member is positioned on a first surface of a target tissue, such as cardiac tissue. The tissue piercing element is then deployed through a first one of the plurality of openings to position a distal end of the tissue piercing element adjacent a second, opposed surface of the target tissue. Once the tissue piercing element is properly positioned, ablative energy is transmitted between the distal end of the tissue piercing element, intervening target tissue, and the conductive member to form a lesion segment in the target tissue. The steps of deploying the tissue piercing element and transmitting ablative energy are repeated at each of the plurality of openings to form a lesion of a desired size and pattern. Preferably, the openings are spaced apart at a distance such that the plurality of lesion segments overlap to form a single, elongate lesion.

In another embodiment, an introducer element is provided having an inner lumen formed therein. A return electrode is also provided and is effective to communicate with a source of ablative energy. The return electrode is movable between a first, retracted position wherein the return electrode is disposed within the inner lumen of the introducer element, and a second, open position wherein the return electrode has a substantially circumferential shape. The introducer element is inserted through a tissue surface with the return electrode in the first, retracted position. The return electrode is then moved to the second, open position. Ablative energy is then transmitted between the energy transmitting electrode, intervening target tissue, and the return electrode while the energy transmitting electrode is moved around the circumference of the return electrode, thereby forming a substantially circumferential lesion.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides surgical ablation systems and methods for treating atrial fibrillation. The system and methods are particularly effective to form a lesion uniformly through the entire thickness of the tissue, e.g. the myocardial wall, without incising the atria. The methods can be performed during open-heart surgical procedures, but are preferably performed using thoracoscopic techniques, wherein the ribs and sternum remain intact and are not significantly retracted during each step of the procedure. The techniques according to the present invention avoid the need for a gross thoracotomy, and offer more control and precision in treating atrial fibrillation.

The system generally includes a first conductive member having a shape which defines a desired lesion pattern or a portion of a desired lesion pattern, and a second conductive member effective to transmit ablative radiation to the first conductive member. The first conductive member is adapted to be positioned on a first tissue surface, and the second conductive member is adapted to be positioned on a second, opposed tissue surface. In use, ablative radiation is transmitted between the second conductive member, the target tissue, and the first conductive member to form a lesion having the desired lesion pattern.

For reference purposes, the tissue surface will be referred to herein as having a first, outer surface, and a second, inner surface. In a preferred embodiment, the tissue is the myocardial wall of a heart having an epicardial outer surface and an endocardial inner surface.

Figure 1:
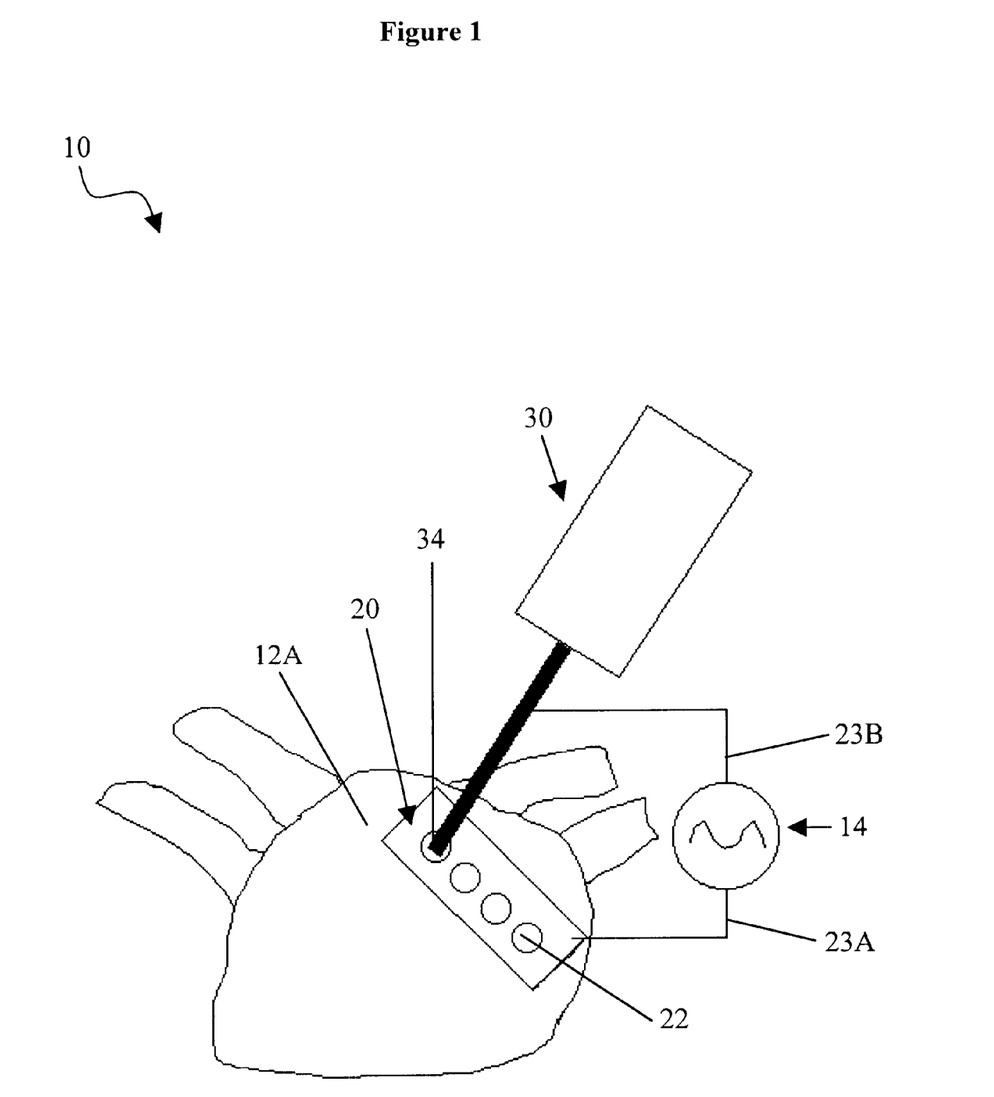
FIG. 1 is an illustration of a surgical ablation system having a conductive member and a tissue piercing element according to one embodiment of the present invention.

FIG. 1 illustrates one embodiment of the system 10 according to the present invention wherein the first conductive member is an elongate conductive member 20, that may be of a plate-like shape, and has a plurality of openings 22 formed therein, and the second conductive member is a tissue piercing element 30 electrically isolated from the elongate conductive member 20. The elongate conductive member 20 and the tissue piercing element 30 are each adapted to communicate with an ablative source of energy 14, and together are effective to ablate tissue. A first conductor element 23A can be provided for electrically communicating between the elongate conductive member 20 and the source of ablative energy 14, and a second conductor element 23B can be provided for electrically communicating between the tissue piercing element 30 and the source of ablative energy 14.

Figure 2A:
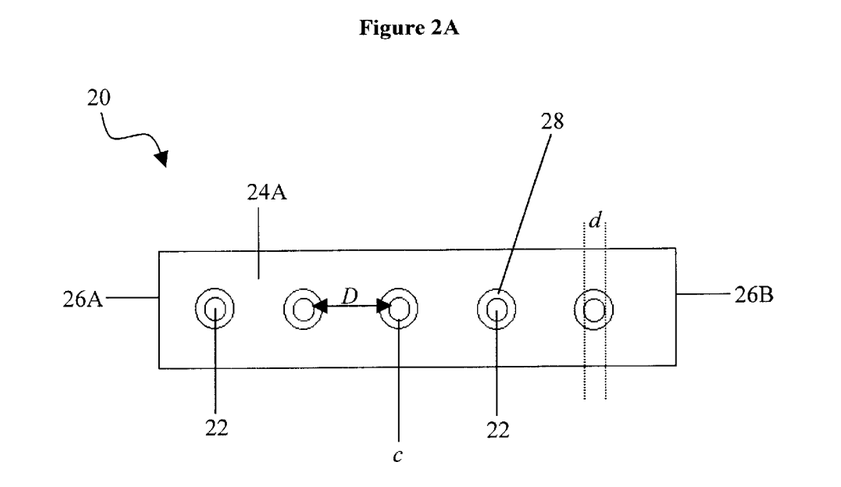
FIG. 2A is a top view of the conductive member of FIG. 1.
Figure 2B:
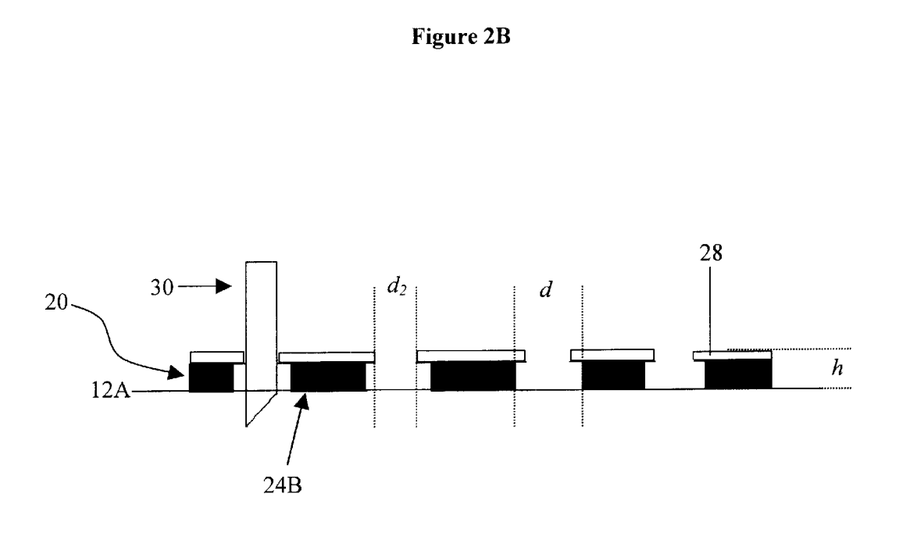
FIG. 2B is a side view of a conductive member according to one embodiment of the present invention.

As shown in FIGS. 2A and 2B, the elongate conductive member 20 can have any shape and size, but preferably has a generally elongate planar shape having a top surface 24A, a bottom surface 24B, a first end 26A, and a second end 26B. The conductive member 20 provides a template for all or part of a lesion, and thus the shape of the conductive member 20 is determinative of the shape or pattern of the lesion, or portion of a lesion, to be formed. In an exemplary embodiment, the conductive member 20 has a preformed shape, and/or is malleable to allow the conductive member 20 to be formed into a desired shape. By way of non-limiting example, the conductive member 20 can be formed to have a curvilinear or circumferential shape to allow the conductive member 20 to be positioned around all of, or a portion of, the pulmonary veins. As a result, the lesion formed in the tissue will have a curvilinear or circumferential shape substantially the same as the shape of the conductive member 20.

The elongate conductive member 20 includes a plurality of openings 22 formed therein and extending between the top and bottom surfaces 24A, 24B. The openings 22 form a template for a lesion pattern to be formed in the tissue. Accordingly, each opening 22 is spaced apart by a distance D, which should be adapted to form a plurality of lesions that overlap to form a single, elongate lesion. Preferably, the distance D between each opening 22 should be substantially the same as or less than the depth of penetration of the tissue piercing element 30, since the depth of penetration of the tissue piercing element 30 (FIG. 1) into the tissue is substantially the same as the length of the lesion to be formed. Thus, for example, where the tissue piercing element (FIG. 1) is penetrated about 5 mm into the tissue, the lesion formed will have a length of about 5 mm, and therefore the distance D between each opening should be about 5mm or less than 5 mm in order to ensure that the lesions overlap to form a single, elongate lesion. In a preferred embodiment, the distance D is between about 2 mm and 10 mm, and more preferably is about 5 mm. Each opening 22 further includes a diameter d and a circumference c, which can vary depending on the diameter $d_t$ (FIG. 3A) of the tissue piercing element 30. The diameter d should be greater than the diameter $d_t$, of the tissue piercing element 30, and preferably is between about 0.01 mm and 5 mm.

The elongate conductive member 20 can be made from any electrically conductive material. Preferred materials include, but are not limited to, stainless steel, titanium and nickel titanium alloys. The length l and width w of the conductive member 20 can vary, but preferably the length l is in the range of about 10 mm to 75 mm and the width w is in the range of about 2 mm to 15 mm. The height h (FIG. 2B) of the conductive member 20, which extends between the top surface 24A and the bottom surface 24B, can also vary, but is preferably in the range of about 0.1 mm to 2 mm.

In use, the elongate conductive member 20 is adapted to be positioned on a first tissue surface 12A. The bottom surface 24B of the conductive member 20 can include an adhesive for temporarily securing the conductive member 20 to the tissue surface 12A. Any biologically compatible adhesive known in the art can be used for this purpose. Examples of suitable adhesives include hydrocolloid adhesives from 3M, and cyanoacrylates. The conductive member 20 can also optionally include a handle (not shown) for positioning the conductive member 20 on a tissue surface 12. Alternatively, or in addition, the conductive member 20 can be mated to a stabilizing mechanism effective to stabilize the heart during beating heart surgery. Stabilizing mechanisms are known in the art and are used to applying a stabilizing force to the heart to minimize the motion of the beating heart during a surgical procedure.

As shown in FIGS. 2A and 2B, the conductive member 20 can include an insulative coating adapted to electrically isolate the tissue piercing element 30 from the elongate conductive member 20. Referring to FIG. 2A, the insulative coating 28 can be disposed around the circumference c of each opening 22 to prevent contact with the tissue piercing element 30 when deployed through an opening 22. Alternatively, as shown in FIG. 2B, the insulative coating 28 can be disposed over the top surface 24A of the conductive member 20 and can include a plurality of openings 25 having a diameter $d_2$ slightly less than the diameter d of the plurality of openings 22 in the conductive member 20. The insulative coating 28 can be formed from a variety of materials. Suitable materials include ultra high molecular weight polyethylene, poly tetra fluoro ethylene (Teflon), nylon, parylene and other biocompatible plastics.

The tissue piercing element 30, which is adapted to be deployed through each of the plurality of openings 22 in the conductive member 20, is effective to transmit ablative energy between the distal end 34 of the tissue piercing element 30, the target tissue 12, and the elongate conductive member 20 to form a lesion segment in the target tissue 12. As shown in FIGS. 1, and 3A–3C, the tissue piercing element 30 is generally an elongate cylindrical member having a proximal end 32, a distal end 34, and optionally at least one inner lumen 36 extending therebetween. The distal end 34 of the tissue piercing element 30 includes a distal, tissue piercing tip 38, e.g. a needle, which is adapted to be deployed into or through a tissue surface, and the proximal end 32 can include a handle 40 for manipulating the tissue piercing element 30.

Figure 3A:
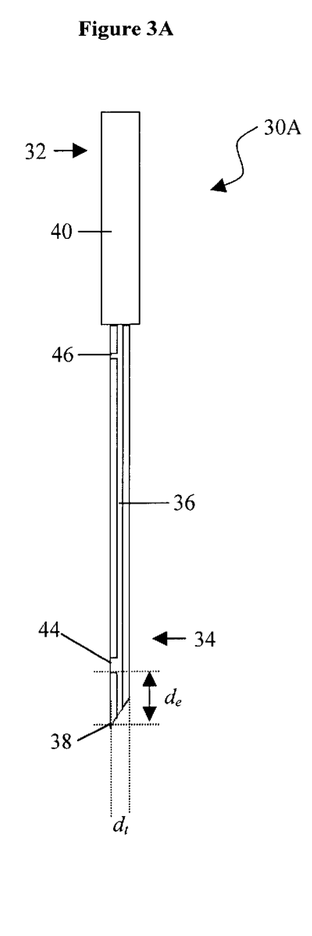
FIG. 3A is a side view illustration of a tissue piercing element having a distal port and an inner lumen according to one embodiment of the present invention.
Figure 3B:
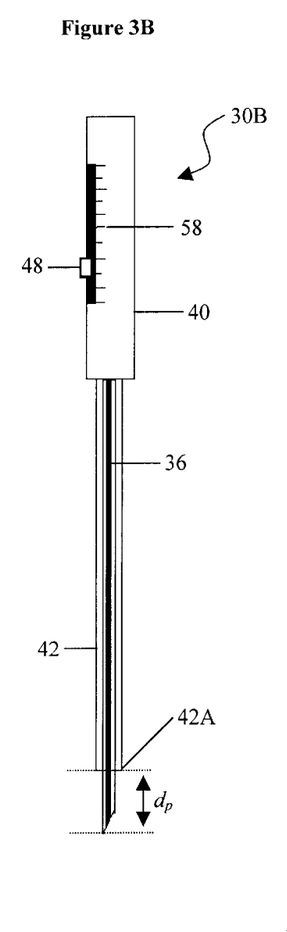
FIG. 3B is a side view illustration of a tissue piercing element having a recessed distal tip and a depth penetration control according to another embodiment of the present invention.

As shown in FIGS. 3A and 3B, the distal tip 38 of the tissue piercing element has a diameter $d_t$ and is adapted to penetrate tissue at a depth $d_p$. The diameter $d_t$, should be less than the diameter d of each opening 22 (FIG. 2A) in the elongate conductive member 22 to allow the tissue piercing element 30, or at least the distal tip 38 of the tissue piercing element 30, to be inserted through each opening 22. Preferably, the diameter $d_t$, is sufficiently small to allow the distal end 38 to puncture the tissue surface 12 without requiring the puncture hole to be sealed after removal of the tissue piercing element 30. Preferably, the diameter $d_t$, is equal to or less than 1 mm.

The penetration depth $d_p$ of the distal tip 38 is dependent on the distance between the openings 22 in the elongate conductive member 20, the desired length of the lesion to be formed in the tissue, as well as the diameters $d_t$, d of the tissue piercing element 30 and each opening 22. As previously indicated, the depth of penetration $d_p$ should be substantially the same as the distance between each opening 22 in the elongate conductive member 20, and consequently the desired length of the lesion to be formed. Preferably, the penetration depth $d_p$ of the distal tip 38 is between about 2 mm and 10 mm, and more preferably is about 5 mm.

Figure 3C:
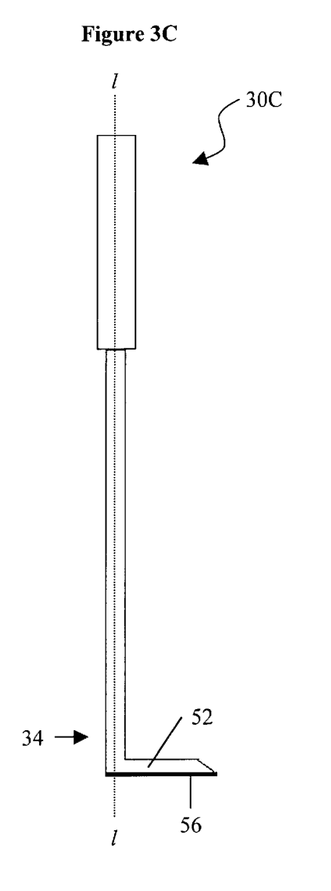
FIG. 3C is a side view illustration of a tissue piercing element having a transverse portion according to yet another embodiment of the present invention.

FIGS. 3A–3C illustrate a variety of different embodiments of the tissue piercing element 30 having different features. A person having ordinary skill in the art will appreciate that the tissue piercing element 30 can include any combination of features illustrated and described herein.

In one embodiment, shown in FIG. 3B, the tissue piercing element can be recessed within a housing 42, and movable between a first position wherein the tip 38 is retracted within the housing 42, and a second position, as shown, wherein the tip 38 extends beyond the distal end 42A of the housing 42. The handle 40 can include an actuating mechanism for actuating the distal tip 38 of the tissue piercing element 30 to move the distal tip 38 from the first position to the second position, thereby deploying the distal tip 38 into or through a tissue surface 12. A variety of actuating mechanisms can be used including, for example, a slidable lever 48, as shown. Other suitable actuating mechanisms include, but are not limited to, spring-actuated pushing assemblies, threaded advancement mechanisms, and pulley assemblies.

In use, the distal end 42A of the housing 42 abuts the outer tissue surface 12A, thereby preventing penetration of the distal tip 38 of the tissue piercing element 30 beyond the penetration depth $d_p$. The distance $d_p$ that the distal tip 38 is moved beyond the distal end 42A of the housing 42 is determinative of the penetration depth, which can be adjustable. By way of non-limiting example, a measurement gauge for adjusting the penetration depth $d_p$ can be provided on the handle 40, as shown in FIG. 3B. The measurement gauge can include a plurality of markings 58 to indicate the penetration depth $d_p$, and the actuating lever 48 can be moved based on the desired penetration depth $d_p$. Alternatively, or in addition, the distal tip 38 of the tissue piercing element 30 can be slidably movable to allow the penetration depth $d_p$ to be adjusted. A person having ordinary skill in the art will appreciate that a variety of different mechanisms can be used to adjust and/or limit the penetration depth $d_p$.

The tissue piercing element 30 can also optionally include a locking mechanism (not shown) for temporarily locking the tissue piercing element 30 in the second, deployed position while ablative energy is delivered to the tissue. The locking mechanism can be, for example, a detent or recess formed in the housing 40 for retaining the actuating lever 48. A person having ordinary skill in the art will appreciate that a variety of different mechanisms can be provided to lock the tissue piercing element 30 in the deployed position.

In another embodiment, shown in FIG. 3A, the tissue piercing element 30A can include a flashback lumen effective to indicate the penetration depth $d_p$ of the distal tip 38 through the tissue. The flashback lumen 36 extends between a distal entry port 44 located at or near the distal end 34 of the tissue piercing element 30A, and an exit port 46 located proximal of the distal entry port 44. In one embodiment, the entry port 44 is located at a particular distance $d_e$ from the distal most tip 38 of the tissue piercing element 30A, and the exit port 46 is disposed near the proximal end 32 of the tissue piercing element 30A, as shown, or in the handle 40, or at some other proximal location. In use, the distal tip 38 is penetrated into tissue, and blood enters the entry port 44 when the entry port 44 is inserted just beyond the thickness of the tissue, thereby indicating the position of the distal tip 38 of the tissue piercing element 30A.

The inner lumen 36 of the tissue piercing element 30A can be used to introduce irrigation and/or cooling fluid to the ablation site. Irrigation fluid is useful for irrigating blood from the ablation site, thereby avoiding or reducing the risk of forming blood clots, and cooling fluid is effective to prevent overheating of the tissue or the formation of hot spots during ablation. Irrigating and/or cooling fluids are known in the art and include, for example, saline, lactated Ringer's solution and sterile water.

FIG. 3C illustrates another embodiment of the tissue piercing element 30C, which includes a transverse portion 52 extending from the distal end 34 of the tissue piercing element 30C in a direction transverse to the longitudinal axis l of the tissue piercing element 30C. The transverse portion 52, when deployed through tissue, is adapted to extend in a direction adjacent to the inner tissue surface 12B. A conductive coating 56 can be disposed around a portion substantially diametrically opposed to the tissue surface to prevent ablative energy from contacting blood flowing adjacent to the inner tissue surface 12B.

A person having ordinary skill in the art will appreciate that the tissue piercing element 30 according to the present invention can include some or all of the aforementioned features. In addition, while an elongate cylindrical member is shown, a person of ordinary skill in the art will appreciate that the tissue piercing element can have any shape and size. By way of non-limiting example, the tissue piercing element can include an array of tissue piercing members, e.g. needles, which are adapted to be disposed simultaneously through each of the plurality of openings in the elongate conductive member 20. Alternatively, the tissue piercing element could be formed integrally with and electrically isolated from the elongate conductive member.

In use, the tissue piercing element 30 is adapted to be disposed through each of the plurality of openings in the elongate conductive member 20, and to apply ablative energy through the tissue 12 to the elongate conductive member 20. In order to prevent contact between the tissue piercing element 30 and the elongate conductive member 20 during insertion of the tissue piercing element 30 through one of the openings 22, the tissue piercing element can optionally include an insulative coating. The coating can be formed around the entire length of the tissue piercing element 30, or a distal portion of the tissue piercing element 30. In the embodiment shown in FIG. 3C, the transverse portion 56 preferably includes an insulative coating formed around a portion of the transverse member substantially diametrically opposed to the inner tissue surface 12B to prevent contact between the transverse portion and any blood flowing adjacent the inner surface 12B of the tissue.

Figure 4:
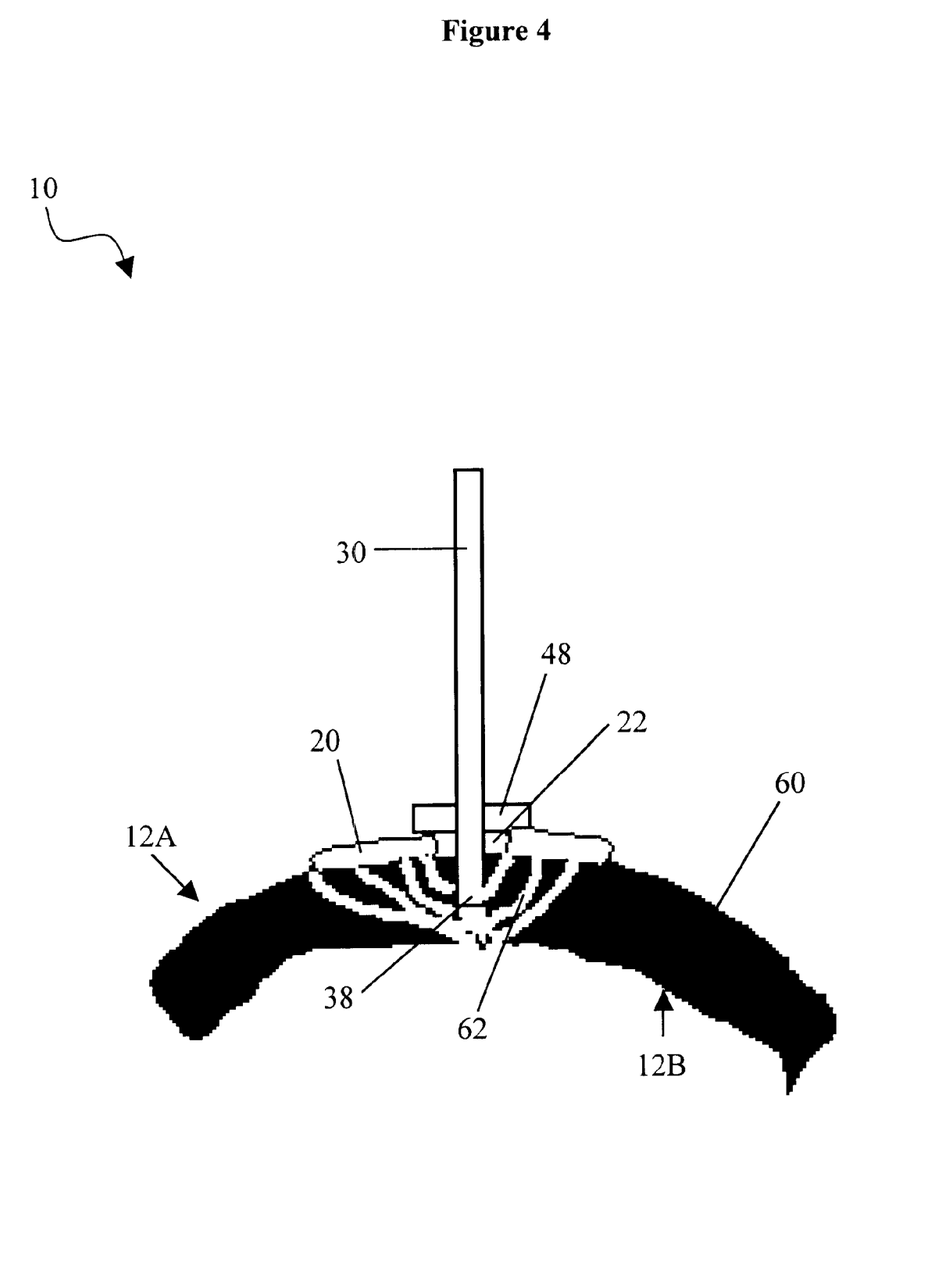
FIG. 4 is an illustration of a surgical ablation system in use having a tissue piercing element transmitting ablative energy through a tissue surface to a conductive member according to one embodiment of the present invention.
Figure 5:
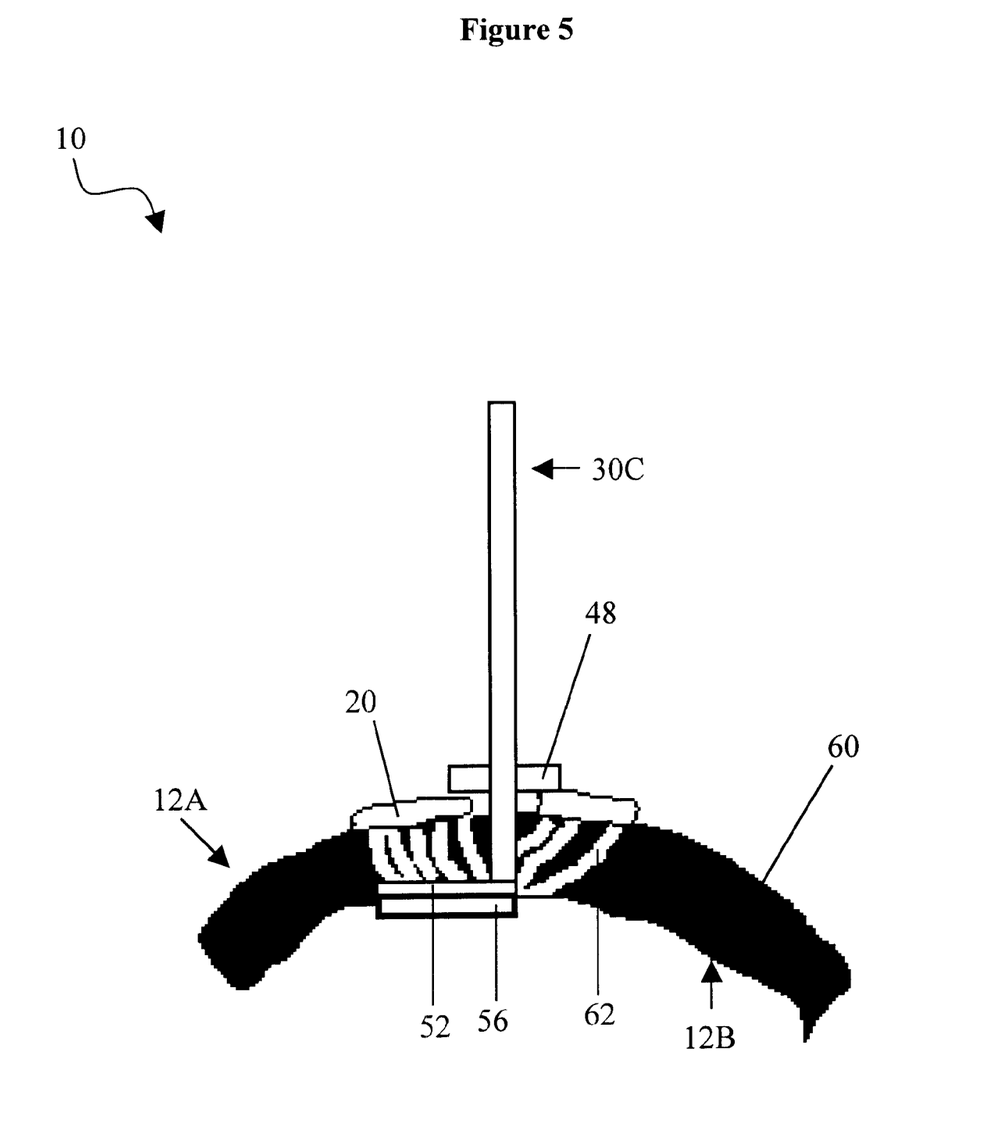
FIG. 5 is an illustration of the tissue piercing element of FIG. 3C in use transmitting ablative energy through a tissue surface to a conductive member according to another embodiment of the present invention.

The system 10 according to the present invention can be used on a stopped or beating heart, and either during open-heart surgery or thoracoscopic heart surgery. The procedure can be performed either alone, or in addition to other surgical procedures. FIG. 4 illustrates a cross-sectional view of the system 10 in use according to one embodiment of the present invention. The elongate member 20, which includes an insulative coating 48 formed around the opening 22, is placed on the outer or epicardial surface 12A of the heart 60. A person having ordinary skill in the art will appreciate that, while the present invention illustrates the elongate member 20 placed on the outer surface 12A of the heart 60, the elongate member 20 can be placed on the inner, endocardial surface of the heart 60. The tissue piercing element 30 is inserted through the opening 22 to position the distal tip 38 at the desired penetration depth $d_p$. Ablative energy 62 is then transmitted between the distal tip 38 of the tissue piercing element 30 and the elongate conductive member 20 to ablate intervening tissue and form a lesion. Where the embodiment shown in FIG. 3C is employed, the distal, transverse member 52 is inserted through the tissue 12 to position the transverse portion 52 adjacent the inner, endocardial surface 12B of the heart, as shown in FIG. 5. The insulative coating 56 is shown positioned substantially diametrically opposed to the tissue surface to prevent contact between the ablative energy 62 and the blood flowing within the heart 60.

The steps of inserting the tissue piercing element 30 through an opening 22 and ablating the tissue are repeated at each of the plurality of openings 22 to form a plurality of lesion segments, which together form a lesion pattern 68. The lesion pattern 68 is preferably formed around the pulmonary veins 64 and connected to the mitral valve 66.

The elongate conductive member 20 can be shaped to fit around the pulmonary veins 64, or it can be moved to form a lesion having the desired pattern.

Figure 6:
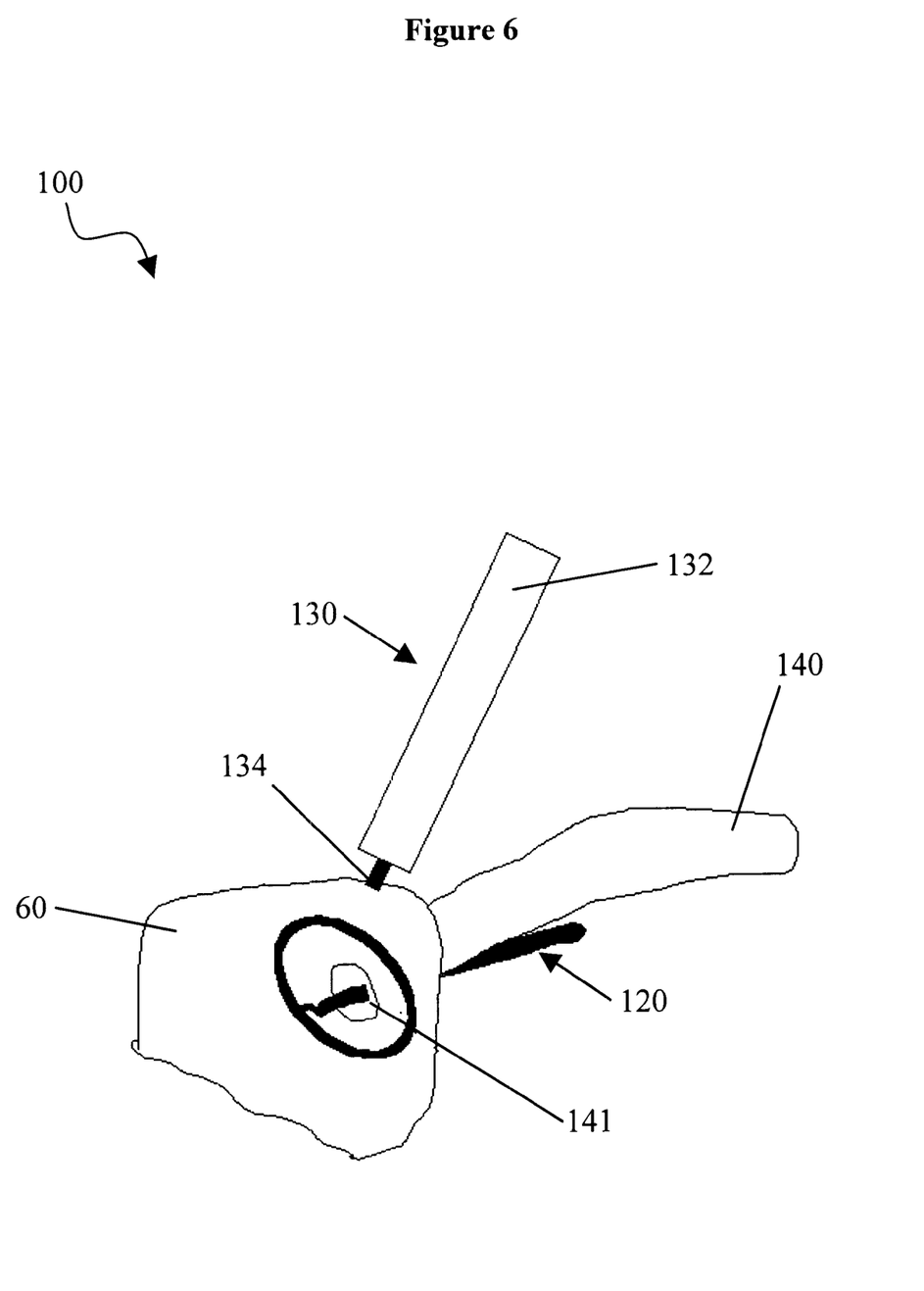
FIG. 6 is a schematic representation of an ablation system having an introducer element inserted through the pulmonary vein of a heart, a return electrode positioned around the ostia of the pulmonary vein, and an energy transmitting electrode positioned on the epicardial surface of the heart according to another embodiment of the present invention.

In another aspect of the invention, shown in FIG. 6, the first conductive member of the system 100 is a return electrode 120 and the second conductive member is an energy transmitting electrode 130. First and second conductors (not shown), e.g. electrically conductive wires, are provided for separately electrically connecting the return electrode 120 and the energy transmitting electrode 130 to a source of ablative energy. The return electrode 120 is movable between a first, retracted position (not shown), and a second, open position, as shown in FIG. 6. In use, the return electrode 120 is adapted to be positioned adjacent a first tissue surface, preferably the endocardial surface of the of a pulmonary vein. The energy transmitting electrode 130 is then moved around a second, opposed tissue surface, preferably the epicardial surface of the ostia 141, while communicating ablative energy between the tissue and the return electrode to form a circumferential lesion.

Figure 7:
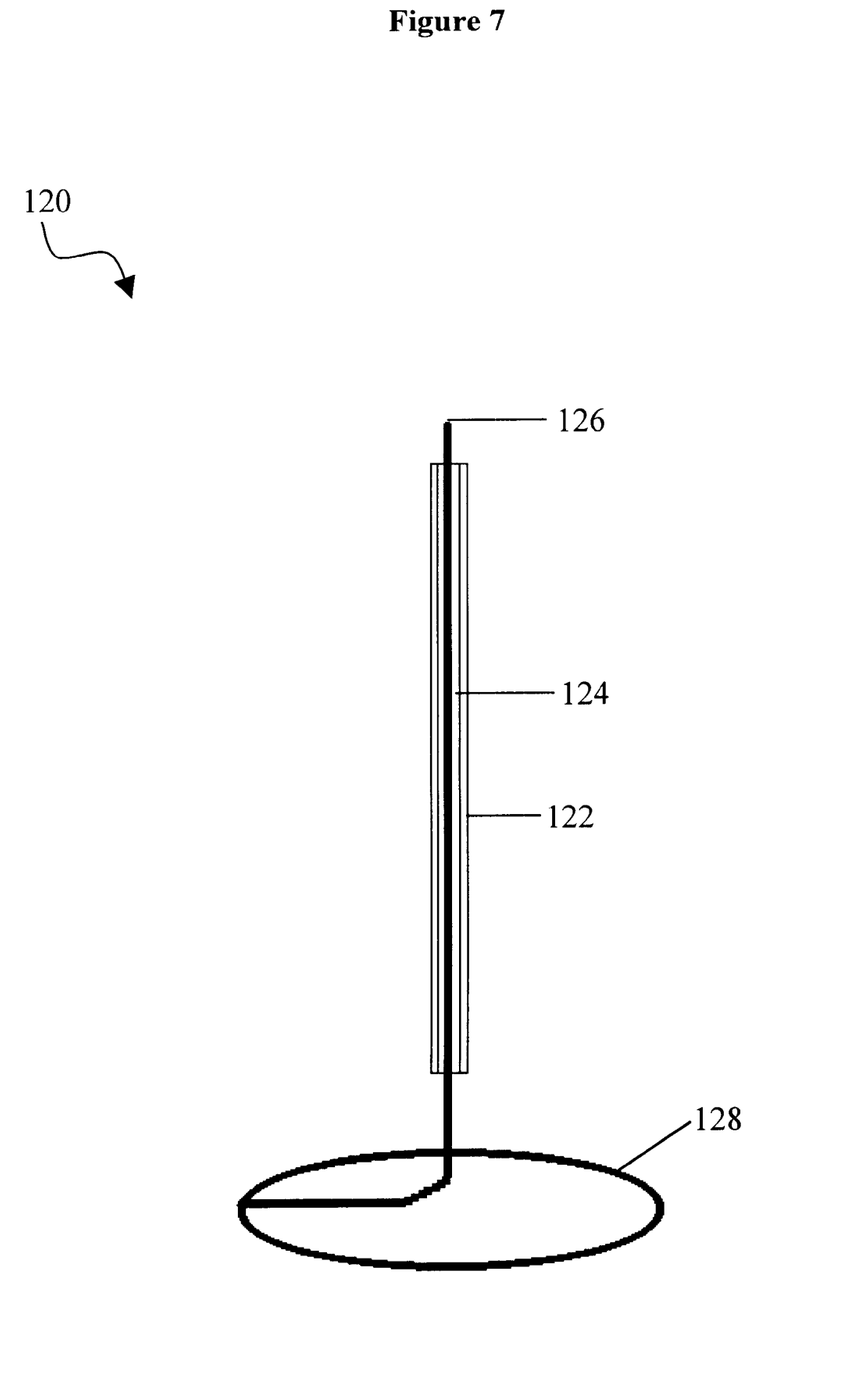
FIG. 7 is a side perspective view of the introducer element and return electrode of FIG. 6.

The return electrode 120 can have a variety of shapes and sizes, but it preferably includes a proximal end 126 and a distal, tissue contacting end 128, as shown in FIG. 7. The proximal portion 126 of the return electrode 120 has an elongate shape, and the distal portion 128 has a circumferential shape. The distal portion 128 is movable between an open, circumferential position, as shown, and a retracted position that enables the return electrode 120 to be inserted through a tissue surface. In a preferred embodiment, the return electrode 120 is formed from a shape memory material and is adapted to collapse into a single, elongate member in the retracted position for inserted or removing the return electrode 120 from a tissue surface. Once fully inserted through or removed from a tissue surface, the return electrode 120 is adapted to expand into the open position. The return electrode 120 can be malleable to allow the shape of the distal portion 128 to be altered based on the desired use.

The return electrode 120 can optionally include a tissue piercing portion or tip in the retracted position for inserting the return electrode 120 through a tissue surface. An actuating mechanism can be provided for positioning the return electrode 120 in the retracted position while inserting and removing the electrode 120 from the tissue. Alternatively, or in addition, an introducer element 122 can be provided for positioning the return electrode 120 adjacent an inner tissue surface. The introducer 122 can be a tissue piercing member, such as a needle, having at least one inner lumen 124 formed therein and adapted to receive the return electrode 120. The return electrode 120 is disposable within the inner lumen of the introducer 122 while in the retracted position, and can be moved to the open position after the introducer 122 is inserted through the tissue.

The return electrode 120 can include an actuating mechanism for moving the return electrode 120 between the open and retracted positions. Preferably, the return electrode 120 is slidably disposable within the inner lumen 124 of the introducer. A handle or similar grasping element can be provided on or near the proximal end 126 of the return electrode 120 to move the return electrode 120 between the open and retracted positions. A person having ordinary skill in the art will appreciate that a variety of different actuating mechanisms can be provided for moving the return electrode 120 between the open and retracted positions.

Referring again to FIG. 6, the energy transmitting electrode 130 can have any shape and size and is adapted to communicate energy through the tissue the return electrode 120. Preferably, the energy transmitting electrode 130 is a pen-like object having a handle 132 and a distal energy transmitting end 134. A conductor (not shown) enables the distal energy transmitting end 134 of the electrode 130 to communicate with a source of ablative energy (not shown).

In use, the return electrode 120 is introduced through a tissue surface, preferably through a pulmonary vein 140, while in the retracted position (not shown). The return electrode 120 can be fully disposed within the inner lumen 124 of the introducer 122 while the introducer 124 is deployed through the tissue, or alternatively the return electrode 120 can be inserted through the introducer 122 after the introducer is inserted through the tissue. The distal end 128 of the return electrode should be positioned just beyond the endocardial surface of the ostia 141 of the pulmonary vein prior to moving the return electrode 120 to the open position. Once opened, the proximal end 126 of the return electrode can be moved proximally to cause the distal, circumferential portion 128 to be positioned adjacent the tissue surrounding the ostia 141 of the vein. The energy transmitting electrode 130 is then moved around the epicardial surface of the ostia 141 of the pulmonary vein while energy is transmitted through the tissue to the return electrode 120, thereby forming a circumferential lesion around the pulmonary vein. A person having ordinary skill in the art will appreciate that the return electrode can be positioned around the epicardial surface of the pulmonary vein, or at any other location on the heart, and the energy transmitting electrode 130 can be positioned at an opposed tissue surface.

One of ordinary skill in the art will appreciate that a variety of electrosurgical generators can be used as the energy source. In one embodiment, the energy source is a radiofrequency (RF) generator that can operate in bipolar and/or monopolar mode. Such a generator should be capable of delivering RF energy having from about 1 to 100 watts of power and a frequency in the range of about 1 KHz to 1 MHz. More preferably, however, the desired frequency is in the range of about 250 KHz to 600 KHz, and the desired wattage is in the range of about 10 to 50 watts.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical ablation system, comprising:
a first conductive member adapted to be positioned on a first tissue surface and having a plurality of spaced apart openings formed therein which together form a portion of a desired lesion pattern, and having a shape which conforms to a portion of desired lesion pattern, the first conductive member being effective to communicate with a source of ablative energy; and
a second conductive member adapted to be positioned adjacent a second, opposed tissue surface and effective to communicate with a source of ablative energy, the second conductive member being effective to transmit ablative energy through the tissue to the first conductive member to form a lesion in a desired lesion pattern.

2. The ablation system of claim 1, wherein:
the first conductive member is an elongate conductive member and each of the plurality of openings has a diameter; and
the second conductive member is a tissue piercing element having a diameter less than the diameter of each opening and being electrically isolated from the elongate conductive member.

3. The ablation system of claim 2, wherein the tissue piercing element includes a proximal end and an energy delivering distal end that is adapted to be selectively deployed into tissue through each of the plurality of openings.

4. The ablation system of claim 3, further comprising:
a first conductor element extending from the elongate conductive member and adapted to communicate with the source of ablative energy; and
a second conductor element extending from the tissue piercing element and adapted to communicate with the source of ablative energy.

5. The ablation system of claim 4, wherein the tissue piercing element is an energy transmitting electrode and the elongate conductive member is a return electrode.

6. The ablation system of claim 4, wherein the elongate conductive member is malleable.

7. The ablation system of claim 4, further comprising an insulative coating disposed around a circumference of each of the plurality of openings in the elongate conductive member.

8. The ablation system of claim 4, further comprising an insulative coating disposed around a portion of the tissue piercing element.

9. The ablation system of claim 4, wherein the tissue piercing element includes a fluid flashback lumen extending between a fluid entry port formed on the distal end of the tissue piercing element and a fluid exit port formed proximal of the fluid entry port.

10. The ablation system of claim 4, wherein the distal end of the tissue piercing element includes a transverse portion which is adapted to be positioned adjacent the elongate conductive member when inserted through one of the plurality of openings.

11. The ablation system of claim 10, wherein a portion of the transverse portion substantially diametrically opposed to the tissue surface is partially coated with an insulative coating.

12. A surgical ablation system, comprising:
a first conductive member adapted to be positioned adjacent a first tissue surface, the first conductive member comprising a return electrode movable between a first, retracted position and a second, open position, the return electrode having a shape substantially in the form of a loop in the open position; and
a second conductive member adapted to be positioned on a second, opposed tissue surface and effective to communicate with a source of ablative energy, the second conductive member having a distal, energy transmitting electrode effective to transmit ablative energy to the first conductive member to form a substantially circumferential lesion pattern.

13. The system of claim 12, further comprising an introducer element having an inner lumen formed therein and adapted to receive the return electrode in the retracted position.

14. The system of claim 13, wherein the return electrode is formed from a shape memory material.

15. A method for ablating tissue, comprising:
providing a conductive member having a plurality of openings and being effective to communicate with a source of ablative energy;
providing a tissue piercing element electrically isolated from the conductive member and effective to communicate with the source of ablative energy;
positioning the conductive member on a first surface of a target tissue;
deploying the tissue piercing element through a first one of the plurality of openings to position a distal end of the tissue piercing element adjacent a second, opposed surface of the target tissue;
communicating ablative energy between the distal end of the tissue piercing element and the conductive member through the tissue to form a lesion segment in the target tissue; and
repeating the steps of deploying and transmitting at each of the plurality of openings to form a plurality of lesion segments which together form a lesion pattern.

16. The method of claim 15, wherein the conductive member includes a first electrical conductor attached to the conductive member and the source of ablative energy, and the tissue piercing element includes a second electrical conductor attached to the tissue piercing element and the source of ablative energy.

17. The method of claim 15, wherein the tissue is cardiac tissue and the conductive member is positioned on an epicardial surface of cardiac tissue, and the tissue piercing element is deployed to position the distal end adjacent an endocardial surface of cardiac tissue.

18. The method of claim 15, wherein the tissue is cardiac tissue and the conductive member is positioned on an endocardial surface of cardiac tissue, and the tissue piercing element is deployed to position the distal end adjacent an epicardial surface of cardiac tissue.

19. A method of ablating tissue, comprising:
providing an introducer element having an inner lumen formed therein, and a return electrode member effective to communicate with a source of ablative energy, the return electrode being movable between a first, retracted position wherein the return electrode is disposed within the inner lumen of the introducer, and a second, open position wherein the return electrode has a substantially circumferential shape;
inserting the introducer element through a tissue surface with the return electrode in the first, retracted position;
moving the return electrode to the second, open position;
providing an energy transmitting electrode having a distal end effective to communicate ablative energy through tissue to the return electrode; and
communicating ablative energy between the energy transmitting electrode and the return electrode through the tissue, while moving the energy transmitting electrode around the circumference of the return electrode, thereby forming a substantially circumferential lesion.

20. The method of claim 19, wherein the introducer element is inserted through a pulmonary vein to position the return electrode around the endocardial surface of the ostia of the pulmonary vein.

* * * * *